(12) United States Patent
Su et al.

(10) Patent No.: US 11,089,705 B2
(45) Date of Patent: Aug. 10, 2021

(54) ELECTRONICS DEVICE HAVING A PLASTIC COVER WITH A SEALED CENTER BOSS

(71) Applicant: Continental Automotive Systems, Inc., Auburn Hills, MI (US)

(72) Inventors: Patrick Su, Shelby Township, MI (US); Kevin D Moore, Bloomfield Hills, MI (US)

(73) Assignee: Continental Automotive Systems, Inc., Auburn Hills, MI (US)

(*) Notice: Subject to any disclaimer, the term of this patent is extended or adjusted under 35 U.S.C. 154(b) by 0 days.

(21) Appl. No.: 16/730,162

(22) Filed: Dec. 30, 2019

(65) Prior Publication Data

US 2021/0204423 A1    Jul. 1, 2021

(51) Int. Cl.
| | |
|---|---|
| *H05K 5/00* | (2006.01) |
| *H05K 5/02* | (2006.01) |
| *H05K 1/18* | (2006.01) |
| *H05K 5/03* | (2006.01) |

(52) U.S. Cl.
CPC ........... *H05K 5/0213* (2013.01); *H05K 1/181* (2013.01); *H05K 5/0004* (2013.01); *H05K 5/006* (2013.01); *H05K 5/0017* (2013.01); *H05K 5/03* (2013.01); *H05K 2201/09063* (2013.01)

(58) Field of Classification Search
USPC ......................................................... 361/752
See application file for complete search history.

(56) References Cited

U.S. PATENT DOCUMENTS

| | | | | |
|---|---|---|---|---|
| 6,366,465 | B1* | 4/2002 | Baur ..................... | H05K 7/142 211/41.17 |
| 8,023,284 | B2* | 9/2011 | Sung ..................... | G06F 1/1601 361/807 |
| 8,526,195 | B2* | 9/2013 | Hublier .................. | H01R 43/04 361/807 |
| 8,937,814 | B2* | 1/2015 | Tu ........................... | G06F 1/184 361/807 |
| 2011/0194264 | A1* | 8/2011 | Hsieh ................... | H05K 7/1405 361/759 |

* cited by examiner

Primary Examiner — Hung S. Bui

(57) ABSTRACT

An electronics unit includes a housing, the housing having a base portion with a post member extending from the base portion. The post member has a through-hole defined through the post member. A printed circuit board is connected to the housing at a plurality of connection points. The printed circuit board includes one or more electric or electronic components disposed thereon and has an aperture. The post member is disposed through the aperture of the printed circuit board. A distal end portion of the post member is larger than a diameter of the aperture so as to fix the printed circuit board to the housing, forming one of the connection points.

14 Claims, 4 Drawing Sheets

ELECTRONICS DEVICE HAVING A PLASTIC COVER WITH A SEALED CENTER BOSS

FIELD OF INVENTION

The present invention generally relates to a housing cover for the housing of an electronics control unit that provides fixation of the printed circuit board to the housing, that provides electrical connection of the PCB to the housing, and that provides the option to seal or vent the enclosure.

BACKGROUND

Electronic control units (ECUs) are typically installed in the engine compartment of a vehicle. The ECU typically controls many of the functions of the vehicle such as the fuel injector drivers, engine operations, etc., by controlling a series of actuators based on input from sensors. Typical control units have a printed circuit board (PCB) that is disposed in a housing. A cover, mounted to the housing, covers the circuit board. The PCB is secured to the housing in order to maintain the PCB in a fixed position. In one existing implementation illustrated in FIG. 1, a housing 1 for a control unit includes a plurality of post members 2 which extend from the housing. Each post member 2 includes a distal end having a dome shape. FIG. 2 illustrates one such post member 2 which extends through an aperture defined in a PCB 3 during the assembly process for the control unit. A downward force is applied to the distal end of post member 2 which deforms or otherwise flattens the distal end of post member 2, as shown in FIG. 3. The flattened distal end of each post member 2 extends around the corresponding aperture of PCB 3, thereby securing PCB 3 to housing 1.

It has been observed that creating the dome-shaped post members 2 may result in cracks being formed along the post members. In addition, the process of deforming or otherwise flattening the dome-shaped post members 2 may itself create cracking along the post members. This may result in the attachment of PCB 3 to housing 1 being less robust and housing 1 no longer providing a seal in the regions around post members 2.

SUMMARY

Example embodiments are generally directed to a method for assembling an electronics device and a resulting electronics device which is relatively simple in design and inexpensive to manufacture.

An example embodiment is directed to an electronics device including a housing and a printed circuit board. The housing has a post member having a through-hole defined therethrough. The printed circuit board is connected to the housing at a plurality of connection points. The printed circuit board includes one or more electric or electronic components disposed thereon. The post member is disposed through an aperture defined on the printed circuit board. A distal end portion of the post member is deformed so as to fix the printed circuit board to the housing at one of the connection points.

In an example embodiment, an adhesive-backed vent material is disposed on an underside of the housing over the through-hole of the post member so as to form a vent for the electronics device.

In an example embodiment, a ball member is disposed in the through-hole of the post member so as to form a seal therewith. In another example embodiment, a sealant material is disposed at least one of over and in the distal end portion of the post member so as to form a seal therewith.

In another example embodiment, a plug member is disposed at least partly in the post member and a seal member is disposed between the plug member and an inner surface of the post member. The seal member forms a seal between the plug member and the post member. The seal member may have a rubber composition.

In one or more example embodiments, the distal end portion of the post member is larger than a diameter of the aperture of the printed circuit board.

In another example embodiment, an adhesive-backed label is disposed on an underside of the housing and over the through-hole of the post member so as to form a seal with the housing.

A method of assembly an electronics device includes obtaining a housing from which extends a post member having a through-hole defined through the post member and base portion, a printed circuit board, and a housing cover. The method further includes securing the printed circuit board to the housing, including positioning the printed circuit board over the housing so that the post member extends through an aperture defined in the printed circuit board, and deforming a distal end portion of the post member which widens the distal end portion of the post member relative to a diameter of the aperture. The method further includes attaching the housing cover to the housing.

In an example embodiment, the method includes placing an adhesive-backed vent material against an outer surface of the housing so as to cover the through-hole. The post member and adhesive-backed vent material provide a vent for the electronics device at an attachment point for the printed circuit board to the housing.

Deforming the distal end portion of the post member may include obtaining a seal member and a plug member, placing the plug member over the distal end portion with the seal member disposed between the plug member and the distal end portion, and pulling the plug member partly through the distal end portion of the post member so that the distal end portion is widened with the plug member being at least partly disposed within the distal end portion. The seal member forms a seal between the distal end portion and the plug member.

The method may further include sealing the distal end portion of the post member with a sealant, or placing a ball-shaped member in the distal end portion to create a seal between the post member and the ball-shaped member.

BRIEF DESCRIPTION OF THE DRAWINGS

Aspects of the invention will be explained in detail below with reference to exemplary embodiments in conjunction with the drawings, in which.

DETAILED DESCRIPTION

The following description of the example embodiment(s) is merely exemplary in nature and is in no way intended to limit the invention, its application, or uses. In the figures and throughout the detailed description, the same reference numbers are used to identify identical or similar elements. For the sake of clarity, the elements are not shown to scale unless otherwise specified.

In general terms, example embodiments are directed to an electronics device in which the PCB is attached within the electronics device housing without screws or the like and which provides for a more robust attachment.

Figure 1:
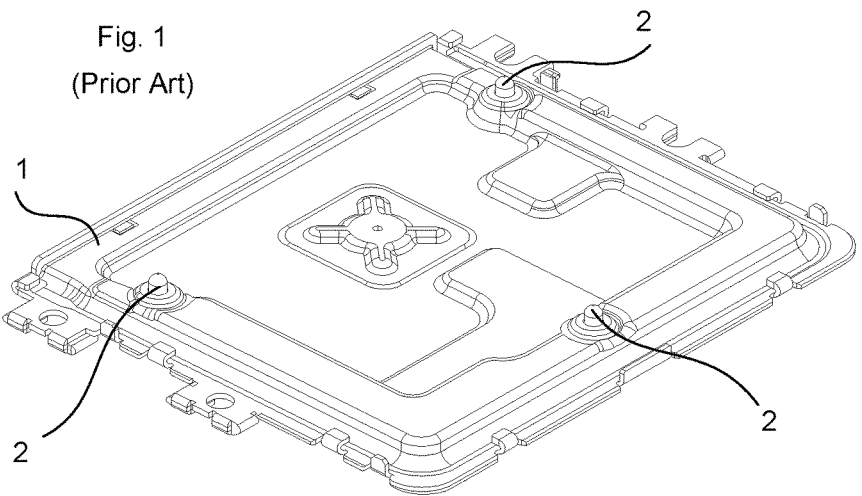
FIG. 1 is a perspective view of at least a portion of a housing used in an existing control unit.
Figure 2:
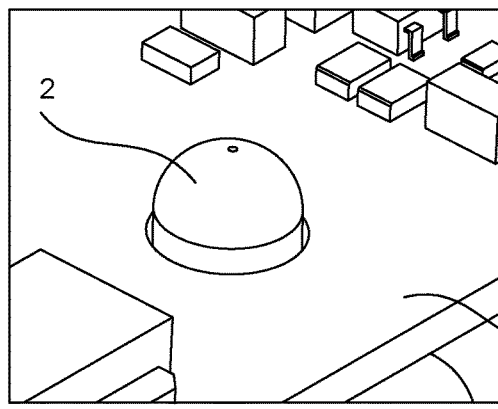
FIG. 2 is a perspective view of a portion of an existing control unit.
Figure 3:
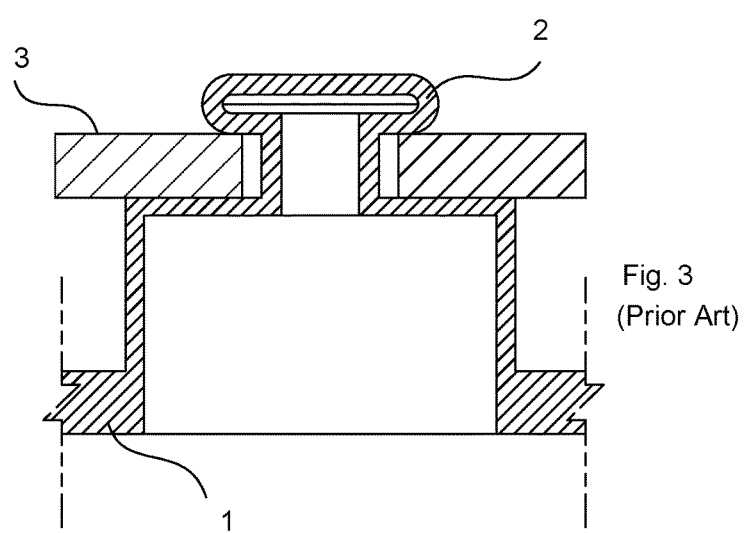
FIG. 3 is a cross-sectional view of a portion of the existing control unit of FIG. 3.
Figure 4:
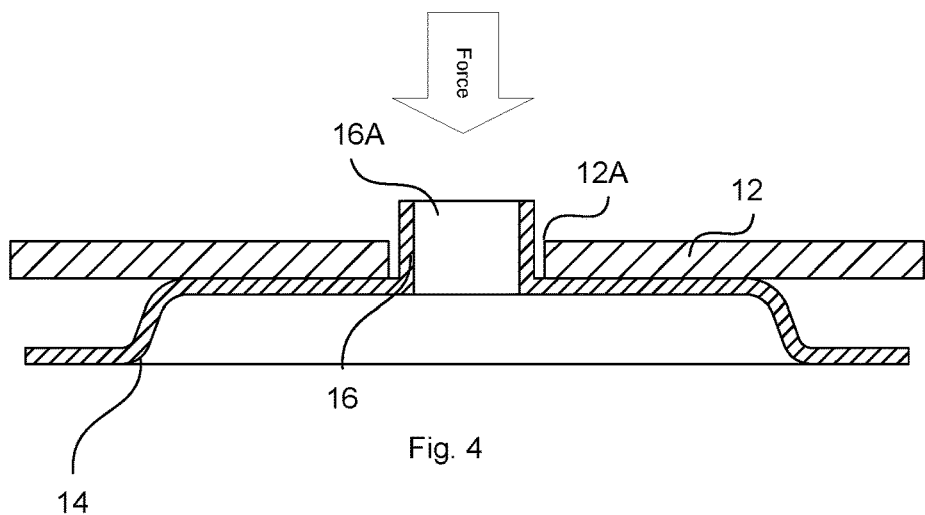
FIGS. 4-6 are cross-sectional views of a portion of an electronics control unit at various stages of assembly according to an example embodiment.
Figure 5:
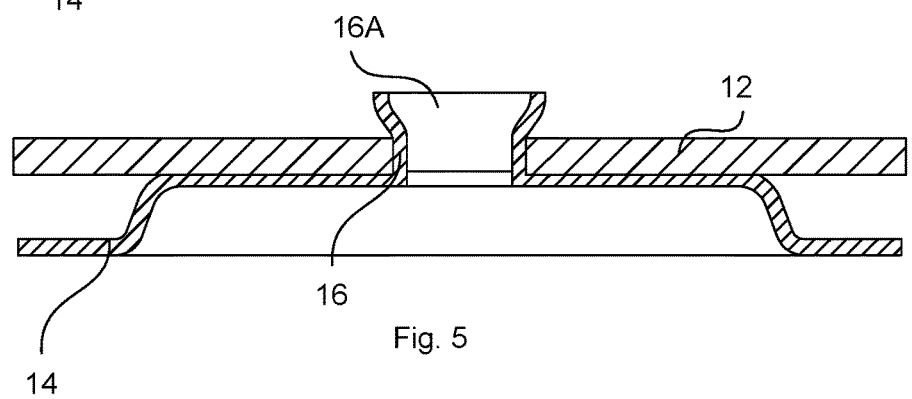

As discussed, FIGS. 1-3 describe a conventional mechanism and method for attaching a PCB within an ECU housing. FIGS. 4-11 illustrate an ECU 10 having an attachment mechanism and method for securing a PCB 12 to a housing 14 according to example embodiments. Whereas the post member in an existing approach has a dome-shaped distal end, in a first example embodiment housing 14 is provided with a post member 16 that is largely cylindrical in shape and has a through-hole 16A defined axially and/or in a lengthwise direction through the post member, thereby resulting in an opening being defined at a first end along housing 14 and at a distal end portion of the post member. Through-hole 16A thus provides an opening through housing 14. Though post member 16 is illustrated as having a cylindrical shape, as shown in FIG. 4, it is understood that post member 16 may have other shapes. Similar to the existing approach, a downward force is applied to the distal end portion of post member 16 so that the distal end portion is deformed. As shown in FIG. 5, the distal end portion of the deformed post member 16 is widened relative to the diameter of post member 16 prior to deformation and relative to aperture 12A through which post member 16 extends. With the deformed distal end portion being wider than the diameter of aperture 12A of PCB 12, post member 16 cannot be moved relative to PCB 12 and PCB 12 is thus attached or otherwise fixed to housing 14. Advantageously, the resulting attachment between PCB 12 and housing 14 does not experience cracks or other defects which may adversely affect the attachment between PCB 12 and housing 14. It is understood that each post member 16 of housing 14 may be shaped and deformed as described.

Figure 6:
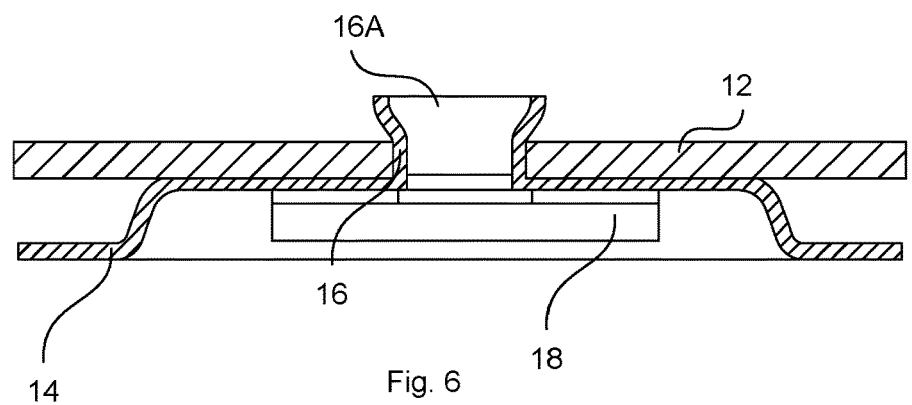

In an example embodiment, in addition to post member 16 serving as a point of attachment between PCB 12 and housing 14, the region of the attachment also serves as a vent for passing air but not liquid into the interior of housing 14. As shown in FIG. 6, an adhesive-backed vent material 18 is disposed along an outer surface of housing 14 so that the material covers the opening at the first end of through-hole 16A. Vent material 18 of this type is known such that a detailed description will not be provided for reasons of simplicity. With vent material 18 disposed around the opening along the outer surface of housing 14 at the first end of through-hole 16A of post member 16, a vent is formed by post member 16 in addition to post member 16 providing a connection point for PCB 12 to housing 14. With this combination of a venting attachment point, other locations devoted solely to providing venting are no longer needed.

Figure 7:
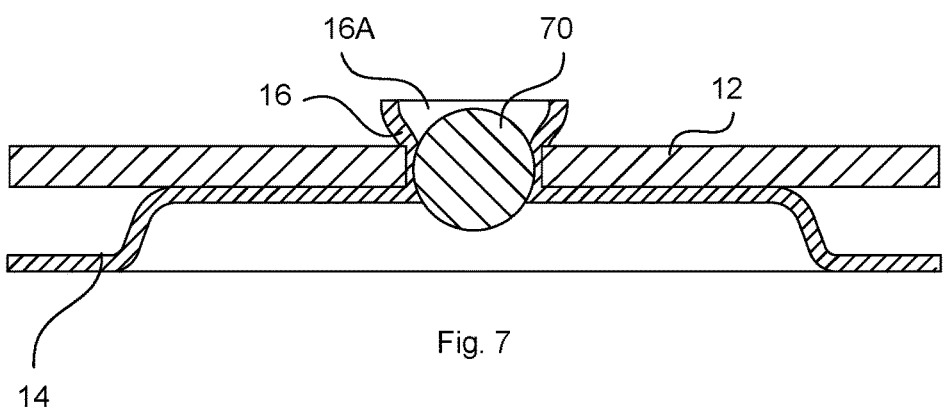
FIG. 7 is a cross-sectional view of a portion of an electronics control unit according to another example embodiment.

Other example embodiments provide for attachment between PCB 12 and housing 14 without additionally providing venting. In one example embodiment, the adhesive-backed vent material 18 is replaced with an adhesive-backed label that is impervious to the passing of air and moisture. In addition, FIG. 7 illustrates an attachment which utilizes the deformed distal end portion of post member 16 as described above. In addition, a rubber ball member 70 is inserted within through-hole 16A of post member 16 so that it engages with the undeformed part of post member 16. Ball member 70 forms a seal with post member 16.

Figure 8:
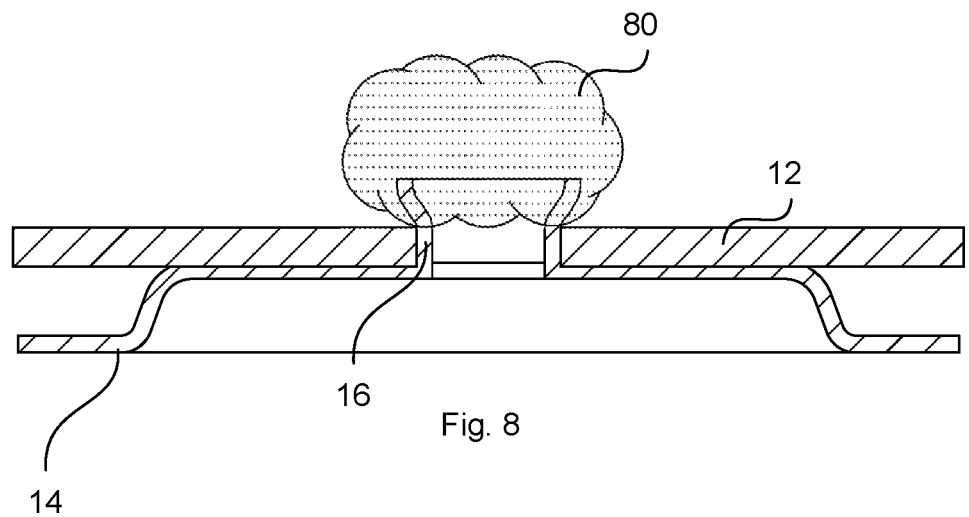
FIG. 8 is a cross-sectional view of a portion of an electronics control unit according to another example embodiment.

FIG. 8 illustrates another example embodiment in which a sealant material 80 is disposed over and/or in the distal end portion of post member 16. Sealant material 80 forms a seal with post member 16.

Figure 9:
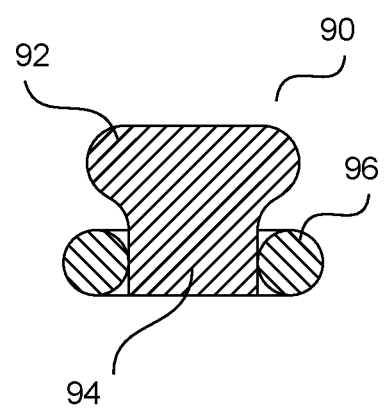
FIGS. 9 and 10 are cross-sectional views of a portion of an electronics control unit according to another example embodiment.
Figure 10:
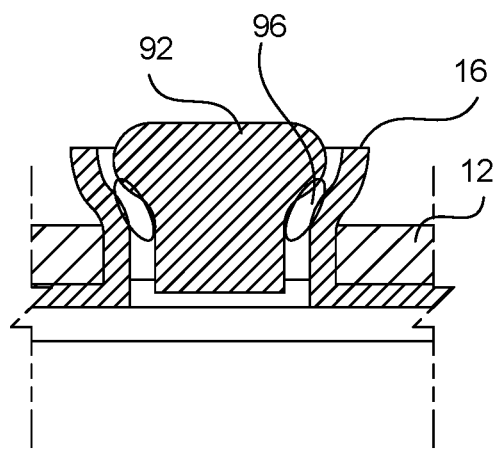

FIGS. 9 and 10 illustrate another approach for attaching PCB 12 with housing 14 in which a pop rivet type of attachment is utilized. In particular, a plug member 90, formed from a rigid, nondeformable material, includes a first portion 92 having an outer dimension, such as an outer diameter, that is larger than the diameter of through-hole 16A of post member 16. A second portion 94 of plug member 90 extends from first portion 92 and has a smaller outer diameter than the diameter of through-hole 16A of post member 16. In addition, a seal member 96, such as an O-ring of a rubber composition or other resilient, compressible material, is disposed around second portion 94. The combination of plug member 90 and seal member 96 is at least partly inserted within the distal end portion of post member 16. A force applied to plug member 90 causes the distal end portion of post member 16 to deform, and in particular to widen, thereby allowing at least part of first portion 92 of plug member 90 to be fixedly disposed within post member 16, as shown in FIG. 10. Second portion 94 of plug member 90 and seal member 96 are disposed within post member 16, with seal member 96 providing a seal with plug member 90 and with post member 16.

Figure 11:
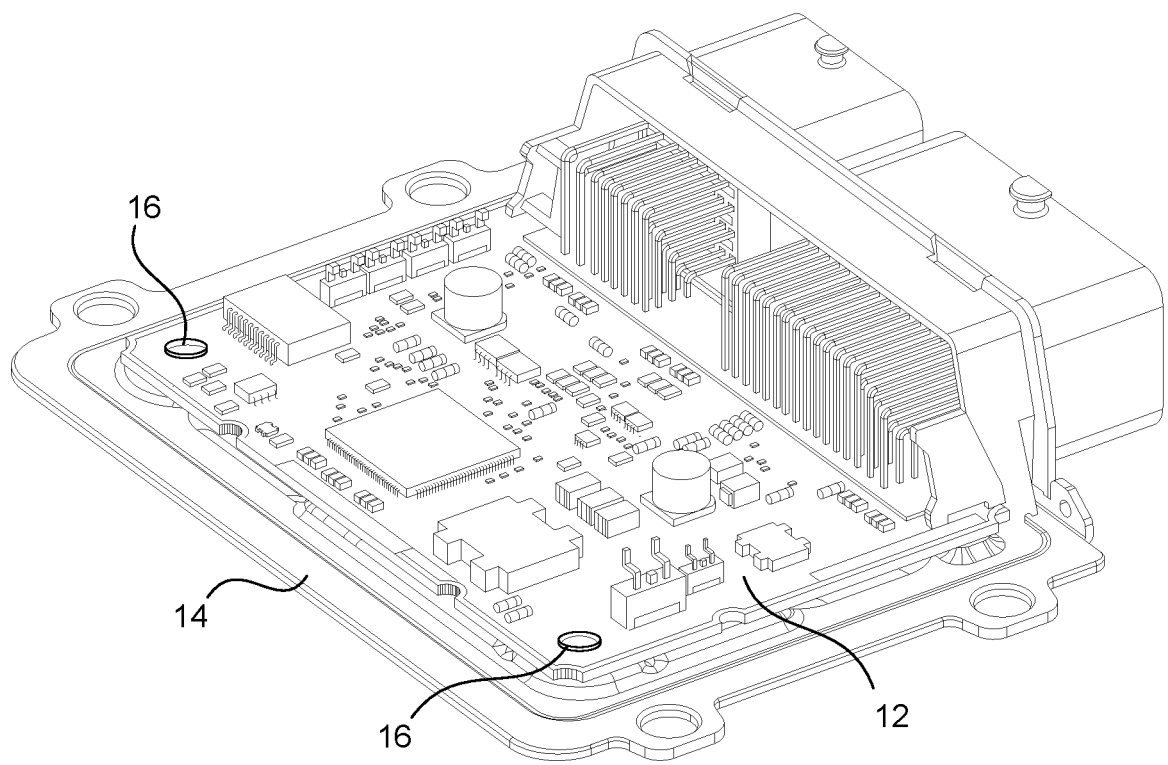
FIG. 11 is a perspective view of at least a portion of an electronics control unit utilizing the example embodiment of FIGS. 4-6.

FIG. 11 is a perspective view of ECU 10 showing the cover of the housing 14 removed. ECU 10 includes two post members 16, the distal end portions of which extend through apertures of PCB 12 for securing PCB 12 to housing 14. Though the example embodiment of FIGS. 4-6 is illustrated in FIG. 11, it is understood that any of example embodiments of FIGS. 7-10 may be utilized in ECU 10.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. An electronics device, comprising:
   a housing, the housing with a post member having a through-hole defined therethrough; and
   a printed circuit board connected to the housing at a plurality of connection points, the printed circuit board including one or more electric or electronic components disposed thereon,
   wherein the post member is disposed through an aperture defined on the printed circuit board, a distal end portion of the post member is deformed so as to fix the printed circuit board to the housing at one of the connection points,
wherein the electronics device further comprises an adhesive-backed material disposed on an underside of the housing over the through-hole of the post member.

2. The electronics device of claim 1, wherein the adhesive-backed material comprises an adhesive-backed vent material disposed on the underside of the housing over the through-hole of the post member so as to form a vent for the electronics device.

3. The electronics device of claim 1, wherein the distal end portion of the post member is larger than a diameter of the aperture of the printed circuit board.

4. The electronics device of claim 1, wherein the adhesive-backed material comprises an adhesive-backed label disposed on the underside of the housing and over the through-hole of the post member so as to form a seal with the housing.

5. The electronics device of claim 1, wherein the housing includes a recess, relative to an exterior of the housing, and the post member and the adhesive-backed material are disposed in the recess.

6. An electronics device, comprising:
a housing, the housing with a post member extending from the housing, the post member having a through-hole defined through the post member; and
a printed circuit board connected to the housing at a plurality of connection points, the printed circuit board including one or more electric or electronic components disposed thereon and having an aperture,
wherein the post member is disposed through the aperture of the printed circuit board, and a distal end portion of the post member is larger than a diameter of the aperture so as to fix the printed circuit board to the housing at one of the connection points,
wherein the electronics device further comprises an adhesive-backed material disposed on an underside of the housing and over the through-hole of the post member.

7. The electronics device of claim 6, wherein the adhesive-backed material comprises an adhesive-backed vent material disposed on the underside of the housing and over the through-hole of the post member so as to form a vent for the electronics device.

8. The electronics device of claim 6, wherein the post member has a deformed section at the distal end portion of the post member.

9. The electronics device of claim 6, wherein the adhesive-backed material comprises an adhesive-backed label disposed on the underside of the housing and over the through-hole of the post member so as to form a seal with the housing.

10. The electronics device of claim 6, wherein the housing includes a recess, relative to an exterior of the housing, and the post member and the adhesive-backed material are disposed in the recess.

11. A method of assembly an electronics device, comprising:
obtaining a housing from which extends a post member having a through-hole defined through the post member and base portion, a printed circuit board, and a housing cover;
securing the printed circuit board to the housing, comprising positioning the printed circuit board over the housing so that the post member extends through an aperture defined in the printed circuit board, and deforming a distal end portion of the post member which widens the distal end portion of the post member relative to a diameter of the aperture;
attaching the housing cover to the housing; and
placing an adhesive-backed material against an outer surface of the housing so as to cover the through-hole.

12. The method of claim 11, wherein placing the adhesive-backed material comprises placing an adhesive-backed vent material against the outer surface of the housing so as to cover the through-hole, the post member and adhesive-backed vent material providing a vent for the electronics device at an attachment point for the printed circuit board to the housing.

13. The method of claim 11, wherein placing the adhesive-backed material comprises placing an adhesive-backed label disposed on the underside of the housing and over the through-hole of the post member so as to form a seal with the housing.

14. The method of claim 11, wherein the housing includes a recess, relative to an exterior of the housing, and the post member and the adhesive-backed material are disposed in the recess.

* * * * *